(12) United States Patent
Schreiber

(10) Patent No.: US 9,651,765 B2
(45) Date of Patent: May 16, 2017

(54) METHOD FOR SEPARATING DETECTION SIGNALS IN THE BEAM PATH OF AN OPTICAL DEVICE

(75) Inventor: Frank Schreiber, Dossenheim (DE)

(73) Assignee: LEICA MICROSYSTEMS CMS GMBH, Wetzlar (DE)

( * ) Notice: Subject to any disclaimer, the term of this patent is extended or adjusted under 35 U.S.C. 154(b) by 1127 days.

(21) Appl. No.: 13/208,387

(22) Filed: Aug. 12, 2011

(65) Prior Publication Data
US 2012/0038907 A1 Feb. 16, 2012

(30) Foreign Application Priority Data

Aug. 13, 2010 (DE) .......................... 10 2010 034 367
Oct. 4, 2010 (DE) .......................... 10 2010 047 237

(51) Int. Cl.
| | | |
|---|---|---|
| *G01N 21/47* | (2006.01) | |
| *G01N 21/55* | (2014.01) | |
| *G01T 1/105* | (2006.01) | |
| *G02B 21/00* | (2006.01) | |
| *G01N 21/64* | (2006.01) | |

(52) U.S. Cl.
CPC ..... *G02B 21/0076* (2013.01); *G02B 21/0084* (2013.01); *G01N 21/6408* (2013.01)

(58) Field of Classification Search
CPC ............ G01N 15/0272; G01N 1/2202; G01N 1/2252; G01N 2001/2223; G01N 21/31; G01N 21/6458; G01N 21/6408; G01J 3/2889; G02B 21/008; G02B 21/0084; G02B 21/0076
USPC .............. 356/73, 73.1, 72, 300, 237.1–237.6
See application file for complete search history.

(56) References Cited

U.S. PATENT DOCUMENTS

| 4,058,732 A * | 11/1977 | Wieder .............. G01N 21/6408 250/461.1 |
|---|---|---|
| 4,198,567 A * | 4/1980 | Eneroth ............. G01N 21/6408 250/459.1 |
| 4,505,586 A | 3/1985 | Tochigi et al. |
| 5,231,464 A * | 7/1993 | Ichimura .............. A61B 5/0059 356/39 |
| 5,323,008 A * | 6/1994 | Studholme ......... G01N 21/6408 250/458.1 |
| 5,792,051 A | 8/1998 | Chance |
| 6,140,048 A | 10/2000 | Müller et al. |
| 6,371,615 B1 | 4/2002 | Schweitzer et al. |
| 6,734,421 B2 * | 5/2004 | Holle et al. .................... 250/287 |

(Continued)

FOREIGN PATENT DOCUMENTS

| DE | 297 11 327 U1 | 11/1997 |
|---|---|---|
| DE | 199 20 158 A1 | 11/2000 |

(Continued)

OTHER PUBLICATIONS

English Machine translation of DE 10038080 Feb. 2002.*

(Continued)

*Primary Examiner* — Kara E Geisel
*Assistant Examiner* — Dominic J. Bologna
(74) *Attorney, Agent, or Firm* — Foley & Lardner LLP

(57) ABSTRACT

A method for separating detection signals in the beam path of an optical device, different signals being formed in a defined temporal sequence, is wherein a suppression or separation of signals is performed on the basis of the temporal sequence which is known or can be determined/established.

12 Claims, 3 Drawing Sheets

(56) References Cited

U.S. PATENT DOCUMENTS

| | | | |
|---|---|---|---|
| 6,791,099 B2 | 9/2004 | Some et al. | |
| 6,965,431 B2 | 11/2005 | Vo-Dinh et al. | |
| 7,170,696 B2 | 1/2007 | Wolleschensky | |
| 7,282,706 B2 * | 10/2007 | Russell et al. | 250/503.1 |
| 7,324,674 B2 | 1/2008 | Ozawa et al. | |
| 7,585,624 B2 | 9/2009 | Fraser et al. | |
| 7,920,259 B2 | 4/2011 | Ernsting | |
| 8,082,024 B2 | 12/2011 | Alfano et al. | |
| 2004/0099813 A1 | 5/2004 | Eggeling et al. | |
| 2006/0061761 A1 | 3/2006 | Li et al. | |
| 2006/0086887 A1 * | 4/2006 | Nakata | G02B 21/0064 250/201.3 |
| 2009/0266999 A1 | 10/2009 | Krattiger | |
| 2010/0032568 A1 | 2/2010 | Fraser et al. | |
| 2011/0007311 A1 | 1/2011 | Correns | |
| 2011/0042580 A1 * | 2/2011 | Wilson | G01N 21/6456 250/458.1 |
| 2011/0122402 A1 | 5/2011 | Westphal | |

FOREIGN PATENT DOCUMENTS

| | | | |
|---|---|---|---|
| DE | 100 38 080 A1 | 2/2002 | |
| DE | 10038080 A1 * | 2/2002 | B82Y 30/00 |
| DE | 10 2004 006 960 A1 | 8/2005 | |
| DE | 603 04 623 T2 | 5/2007 | |
| DE | 10 2005 020 003 B4 | 10/2007 | |
| DE | 603 17 049 T2 | 7/2008 | |
| DE | 602 24 684 T2 | 1/2009 | |
| DE | 10 2008 018 475 A1 | 10/2009 | |
| DE | 10 2008 018 637 A1 | 10/2009 | |
| DE | 10 2009 010 446 A1 | 9/2010 | |
| DE | 10 2006 039 425 B4 | 3/2011 | |
| EP | 0 345 949 A2 | 12/1989 | |
| EP | 1 343 001 A1 | 9/2003 | |
| JP | 7-505467 A | 6/1995 | |
| JP | 2000-500874 A | 1/2000 | |
| JP | 2005-266705 A | 9/2005 | |
| JP | 2006-330685 A | 12/2006 | |
| JP | 2007-525261 A | 9/2007 | |
| JP | 2010-113062 A | 5/2010 | |
| WO | WO 93/19358 A1 | 9/1993 | |
| WO | WO 98/09154 A1 | 3/1998 | |
| WO | WO 00/25114 A1 | 5/2000 | |
| WO | WO 02/16911 A1 | 2/2002 | |
| WO | WO 2004/065944 A2 | 8/2004 | |
| WO | WO 2004/079351 A1 | 9/2004 | |
| WO | WO 2005/069887 A2 | 8/2005 | |
| WO | WO 2008/028298 A1 | 3/2008 | |
| WO | WO 2009/109307 A1 | 9/2009 | |

OTHER PUBLICATIONS

P. Urayama et al., A UV-Visible-NIR Fluorescence Lifetime Imaging Microscope for Laser-based Biological Sensing With Picosecond Resolution, Applied Physics B 76, 2003, pp. 483-496.

J. B. Marques Novo et al., Optimization of a Boxcar Integrator/Averager System for Excited-State Lifetime Measurements, Applied Spectroscopy vol. 46, No. 5, May 1992, pp. 852-859.

Chinese Office Action, Oct. 23, 2014, 10 pages.

Translation of JP 5191352.

Japanese Office Action, Mar. 22, 2016, 4 pages.

* cited by examiner

METHOD FOR SEPARATING DETECTION SIGNALS IN THE BEAM PATH OF AN OPTICAL DEVICE

CROSS-REFERENCE TO RELATED PATENT APPLICATIONS

The right of foreign priority is claimed under 35 U.S.C. §119(a) based on Federal Republic of Germany Application No. 10 2010 034 367.6 filed Aug. 13, 2010, and Federal Republic of Germany Application No. 10 2010 047 237.9, filed Oct. 4, 2010, the entire contents of which, including the specifications, drawings, claims and abstracts, are incorporated herein by reference.

BACKGROUND OF THE INVENTION

The invention relates to a method for separating detection signals in the beam path of an optical device, different signals being formed in a defined temporal sequence.

In quite general terms, what is involved here is a method for separating detection signals in the beam path of an optical device irrespective of the particular application/use. It is essential here that detection signals of different origin and quality are formed in a temporal sequence. The optical device can be, for example, a fluorescence microscope, in particular a confocal laser microscope. Biological samples are marked with appropriate dyes for use in fluorescence microscopy. Said dyes are usually excited to emission with laser light. The fluorescent light is detected for the purpose of imaging.

Reflections which are formed directly on the sample surface and in the transition of the excitation light from one optical medium to another, for example from air to glass or vice versa, are disadvantageous. In the final analysis, interfering scattered light is produced here.

Furthermore, there is the problem that the fluorescent light is approximately 1 million times weaker than the exciting laser light.

This means that for imaging purposes it is essential to separate the reflected excitation light and/or scattered light and fluorescent light and/or their signals as efficiently as possible from one another.

It may be noted at this juncture that the fundamental concern here is the separation of detection signals in the beam path of an optical device, and that fluorescence microscopy is mentioned merely by way of example. The inventive method can therefore always be applied when what is involved is the separation of "mixed" detection signals which are formed in a defined temporal sequence.

Different methods are known from practice for separating the excitation/scattered light from the fluorescent light required for imaging or evaluation, that is to say for separating their signals, in the case of the previously mentioned example, that is to say in fluorescence microscopy. Beam splitters or acousto-optical elements are used for this purpose in the detection beam path. Use is made of the possibility of distinguishing excitation/scattered light and fluorescent light by means of their mutually shifted wavelengths. It is essential in this case that the fluorescent light usually has a larger wavelength than the scattered light.

Again, it is already customary in practice to minimize the undesired reflections by means of an antireflection coating on optical components, in particular on glasses. This—passive—measure permits the reduction of the proportion of the reflected light from a few percent to a few tenths of a percent. However, this is not sufficient.

Furthermore, it is known from practice to suppress the undesired reflected light by means of optical notch filters. These filters likewise use the shifting of the wavelengths in the case of reflected/scattered light and fluorescent light. When notch filters are used, suppression of the reflected/scattered light reaches an optical density of to 8 and more, an optical density of 7 corresponding to a transmission of approximately 0.00001%. At the same time, the transmission of the fluorescent light is up to or over 99%.

SUMMARY OF THE INVENTION

In the light of the above statements, the methods known from practice can be used in the case of fixed excitation wavelengths for the efficient separation of the interfering reflected/scattered light from the fluorescent light which is of interest. However, if use is made of systems with a plurality of defined laser lines in the case of which excitation is performed sequentially or even simultaneously with a plurality of wavelengths, the abovementioned methods are insufficient. The reason for this is to be ascribed to the fact that reflection signals can lie in the fluorescence band of the dyes. In this case, filtering or separation leads to losses of fluorescence signals. Moreover, combinations of notch filters and beam splitters would be required here. This increases the costs of an appropriate device very considerably. Moreover, the efficiency is regularly insufficient in the case of closely adjacent lines.

Disadvantages occur, in particular, when use is made of so-called white light lasers, whose increasing use is to be ascribed to the fact that their wavelength can be set as desired in a specific region, for example in the region between 470 nm and 670 nm. A variable and in this case efficient suppression of the reflected/scattered light cannot be implemented in accordance with existing prior art, the more so as notch filters have so far been available exclusively for fixed or defined wavelengths.

It is therefore one object of the present invention to specify a method for separating detection signals in the beam path of an optical device, in accordance with which simple equipment can be used for satisfactory separation of definable detection signals or definable ranges of the detection signals in conjunction with a good efficiency of the component signals of interest.

The above object is achieved by the features described herein. Accordingly, the generic method is based on a particular situation in accordance with which, specifically, different signals are formed in a defined temporal sequence in the beam path of an optical device. The inventive method is wherein a suppression or separation of signals is performed on the basis of the temporal sequence which is known or can be determined/established, so that the separated signals of interest can be used with sufficiently good efficiency for further purposes.

It may be remarked once more that what is involved in principle here is the separation of detection signals on the basis of the temporal sequence of their formation. The way in which the temporal sequence of the detection signals comes about initially plays no role in this case. The purpose for which the separation of the signals is performed also plays no role.

By contrast with the methods known from practice, the approach here is to operate as a function of time, specifically through knowledge or determination of the temporal sequence of the different signals.

The detection signals can be signals of any type in principle. There are numerous particular applications in accordance with which the detection signals are fluorescent light and reflected light/scattered light, the problem of the separation being of very particular importance there in the light of the preceding statements.

Correspondingly, in accordance with the inventive method a sample suitable for emitting fluorescent light can be excited by pulsed excitation light, so that a defined temporal sequence of fluorescent light and reflected/scattered light is to be expected on the basis of the pulsed excitation. In any event, fluorescent light is emitted from the sample and reflected/scattered light is scattered on the sample and on or in the optical system. Both fluorescence signals and reflection signals are formed in a temporally defined sequence relative to the pulse of the excitation light, so that the separation of fluorescent light and excitation light can be performed on the basis of the temporal sequence of the signals, that is to say by temporal separation.

The fluorescence signals can be used for different applications. Thus, the fluorescence signals can be used for measurements, for example in the field of fluorescence correlation spectroscopy (FCS). Fluctuations in the fluorescence intensity can be used to obtain information in the course of such an application. Diffusion constants, concentrations and connections between various diffusing species can, for example, be measured. A confocal fluorescence microscope is applied here.

It is likewise possible to use the fluorescence signals for fluorescence lifetime microscopy (FLIM technique), specifically by using ion-sensitive fluorescence dyes. What is involved here is the measurement of intracellular ion concentrations in the sample. Use is made in this case of the finding that the fluorescence lifetime, the average dwell time of the electrons in the excited state, changes with the ion concentration.

In a very particularly advantageous way, the separated or cleaned fluorescence signals can be used for imaging, in particular in preferably confocal fluorescence microscopy. What is involved here is a high resolution imaging employing the emissivity of dye-doped samples.

In principle, for the purpose of applying the inventive method it is possible to implement an arrangement, particularly in fluorescence microscopy, in accordance with which the fluorescent light and the reflected light strike a detector in the detection beam path, that is to say in a fashion coming from the fluorescence sample via the optical system. Photons impinging there are converted into electrical signals and can be integrated or summed in a downstream integrator and assigned to pixels for imaging. Thus, the inventive method differs from the prior art by virtue of the fact that the reflection signals are separated or filtered out downstream of the detector, in particular between the detector and the integrator. As already previously described, they are filtered out or separated in a temporal sequence, specifically with knowledge of the temporal sequence of the fluorescence signals and of the reflected/scattered light signals.

In a very particularly advantageous way, the reflection signals can be filtered out or separated from the fluorescence signals via a gate whose function is synchronized with the pulses of the excitation light. In other words, the pulses of the excitation light serve to drive the component effecting the separation or the filtering out, it being possible in principle for signals which are not required or are interfering, for example reflection signals, to be filtered out completely, or else for different signals to be separated from one another in order to feed them to independent integrators, for example.

The purpose of synchronization can be served by a particular synchronization signal which is tapped directly at the laser driver. It is likewise conceivable to determine the detection signal indirectly or directly, for example via a detector, in particular via a fast photodiode. This is known directly from the excitation light or from a fraction of the excitation light. In the final analysis, measurements are made by or with the excitation light.

In a further advantageous way, the gating signal is temporally calibrated to the fluorescence signal in order, specifically, to be able to implement a unique signal selection and assignment of the subsequent detection. The calibration of the gating signal can be performed in a very particularly simple way by adapting the cable length between laser, or a photodiode, and the gate, or a switch. In particular, the term "gating signal" is to be understood in the widest sense, specifically very generally with reference to the driving of a device effecting the separation or the filtering out.

It is also conceivable for the gating signal to be calibrated by a preferably variable electronic delay of the synchronization signal, specifically by using an appropriate electronic device. Such a temporal calibration of the gating signal can be set individually by application, specifically by using an appropriate electronic system.

Additionally, or as an alternative, it is also conceivable for the electronic synchronization signal to be changed by means of software by the user or automatically. This can be done in the course of an optimization.

It is conceivable in principle for one detector or two or more detectors to be driven with the aid of a single synchronization signal. Particularly whenever different signals are to be further processed—in different ways—it is advantageous when at least two synchronization signals are provided in order to supply at least two detectors with different detection light or to actually filter out or separate the signals determined for the respective detectors, and only these signals, and feed them to the detectors.

With reference to fluorescence microscopy, it is important for the inventive method that the light source operates in a pulsed fashion. It is a further advantage here when an alternately pulsed light source is used as light source, specifically to be able to generate detection signals of different type and quality. The required synchronization signals may be tapped or generated in accordance with the previous statements.

It has already been stated at the beginning that inherent to the use of white light lasers is the advantage that their wavelength can be set virtually arbitrarily in a specific region. Consequently, the white light laser offers the enormous advantage of flexibility in the excitation, more specifically owing to the fact that it is possible to use different wavelength regions for illumination and/or excitation.

It is advantageous, furthermore, when excitation is performed sequentially or simultaneously with a plurality of defined laser lines, so that to this extent maximum flexibility of the device employing the method is also ensured.

Photon-counting detectors can be used for detecting the light signals, for example the fluorescence signal in the case of fluorescence microscopy. Photomultipliers can likewise be used. Arbitrary types of detectors can be used in accordance with the particular requirement.

Avalanche photodiodes (APDs) can also be used as detectors.

The triggering of the gating signal can be performed on an edge of the photon-counting signal.

It is also possible to use a constant fraction discriminator in order to achieve temporal triggering that is independent of the signal level, more particularly when using PMTs.

Variably setting the gating period is likewise possible for optimum adaptation to the respective application and, to this extent, of particular advantage.

Instead of a gate, it is also possible to use a filter in order, specifically, to separate the signals instead of suppressing them. Thus, reflection signals of fluorescence signals or differing colors can be separated in conjunction with alternating excitation.

Further objects, features and advantages of the present invention will become apparent from the detailed description of preferred embodiments that follows, when considered together with the accompanying figures of drawing.

BRIEF DESCRIPTION OF THE DRAWINGS

There now exist various options for embodying and developing the teaching of the present invention in an advantageous way. To this end, reference may be made, on the one hand, to the patent claims depending on Patent Claim 1 and, on the other hand, to the following explanation of preferred embodiments of the invention with the aid of the drawing. Generally preferred embodiments and developments of the teaching are also explained in conjunction with the explanation of the preferred embodiments of the invention with the aid of the drawing, in which:

DETAILED DESCRIPTION OF THE PREFERRED EMBODIMENTS

Figure 1:
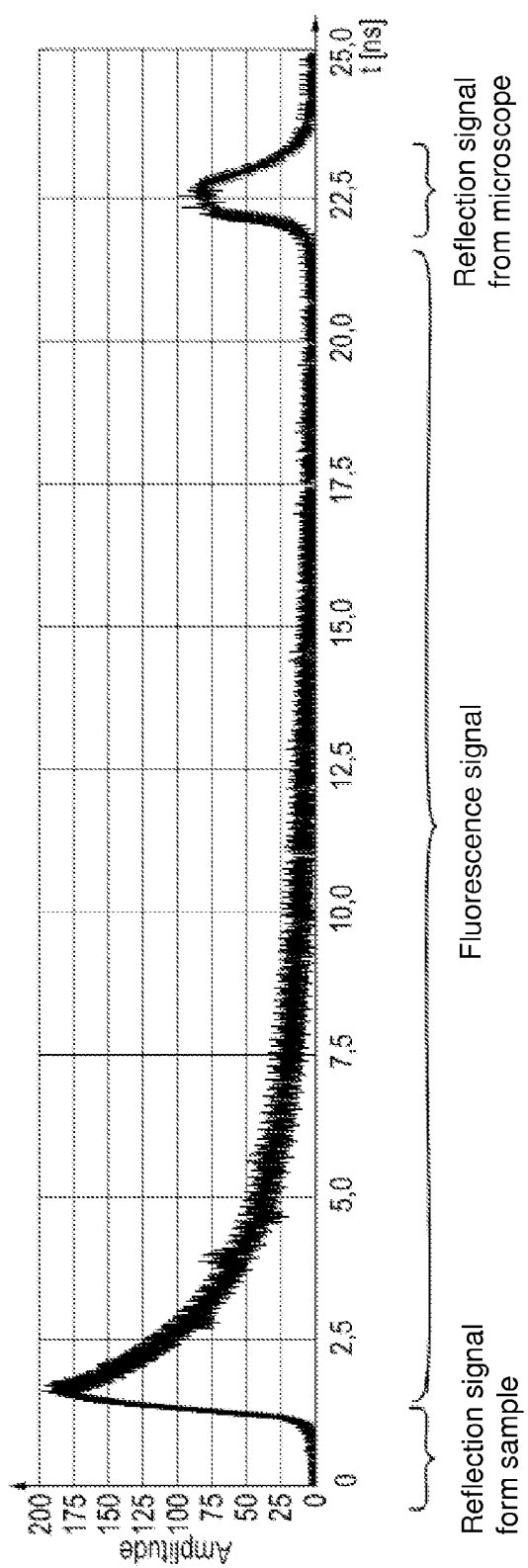
FIG. 1 shows, in a schematic diagram, the periodically repeating temporal sequence of detected reflection signal and fluorescence signal in a confocal microscope.

FIG. 1 shows, in a schematic diagram, the periodically repeating temporal sequence of the respectively detected reflected/scattered light signal and of the fluorescence signal as said signals appear in a confocal fluorescence microscope. The diagram is self-explanatory. It begins with the reflection signal from the sample. This is followed by the fluorescence signal, which flattens out continuously over the time period and is then followed by a reflection signal from the microscope, which reflection signal is to be understood as prepulse to the next main pulse or reflection signal. In the final analysis, what is involved here is a continuous representation with a periodically recurring sequence.

It is important for the representation in FIG. 1 that both the fluorescence signal and reflection signal have a temporally fixed spacing from the excitation laser pulse. It follows that it is possible in a way according to the invention to use the temporal sequence that is known, or can be determined or established, of the respective pulses to suppress or separate the respective signals, specifically irrespective of the fact that what is involved here in concrete terms is reflection signals and fluorescence signals in the case of confocal fluorescence microscopy or, otherwise, defined different signals which can be temporally separated.

Figure 2:
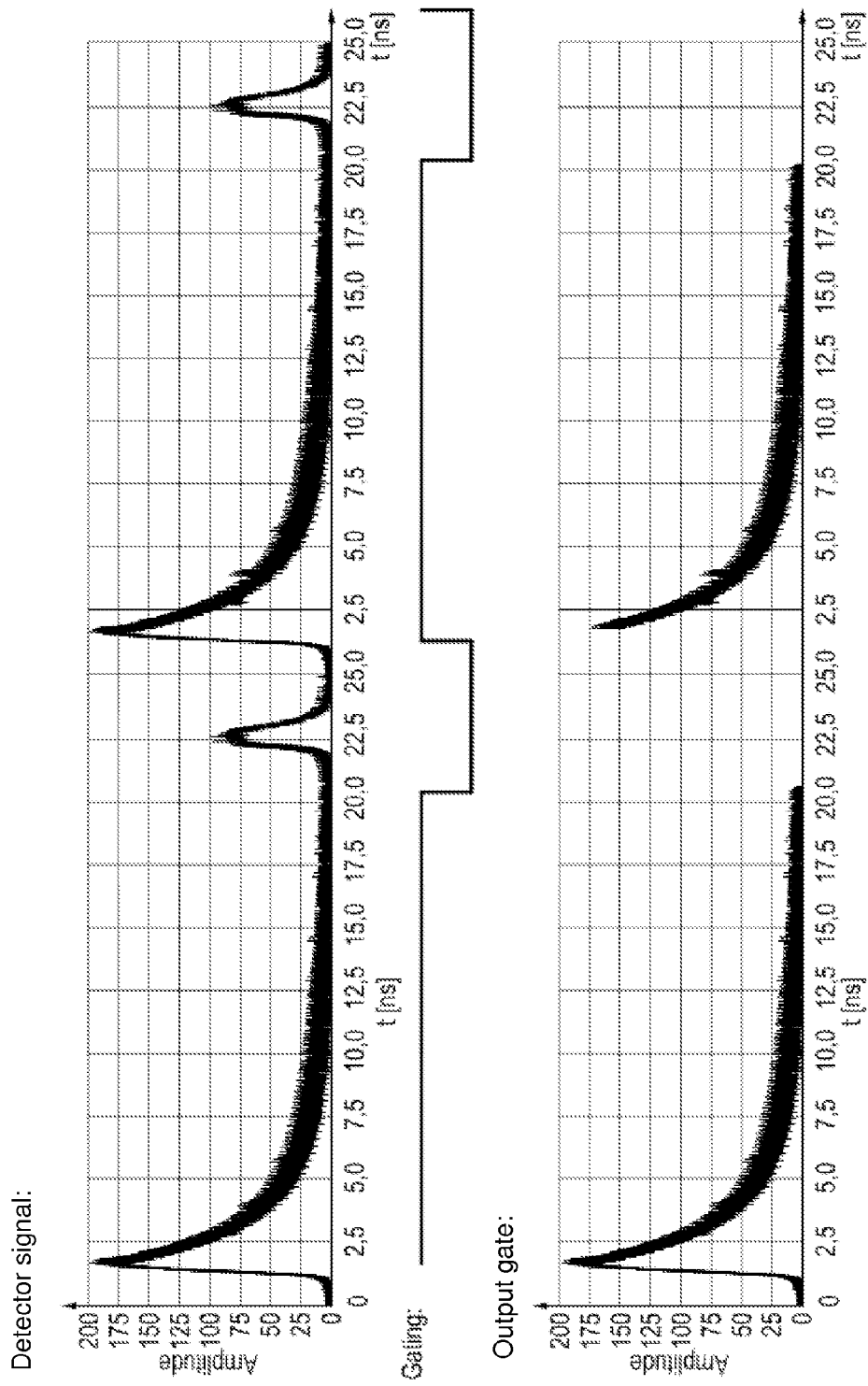
FIG. 2 shows, in schematic diagrams one under another, the periodically repeating temporal signal sequence in accordance with FIG. 1, the profile of the control signal for the gating, and the output signal of the gate

In the upper diagram, FIG. 2 shows the periodically repeating temporal sequence in accordance with FIG. 1 with two periods. What is involved in the final analysis is the detection signal. Electrical signals resulting from the detection signal are gated in accordance with a control signal. This signal, which is responsible for the gating, is shown below in the diagram.

In accordance with the implemented gating and on the basis of a synchronization signal determined, for example, directly from the excitation light, it is possible to define an output at the gate such as is illustrated in the lower diagram, to be specific only the fluorescence component or the fluorescence signal with its decaying curve remaining.

It may be remarked once again at this juncture that, in addition to the suppression of reflection by gating, other applications are also possible in conjunction with the inventive teaching. Thus, for example, alternating light sources, for example having a red laser and a blue laser can be combined in an outstanding fashion in alternating pulsed mode, the respective fluorescence signals being separable from one another. Thus, two signals can be detected independently of one another with only one detector. Instead of suppressing the signal at selected times by gating, the signals are split here between two integrators in a temporally dependent fashion via a filter.

Cross-talk signals can be reduced. Thus, a certain proportion of for example, blue laser light additionally excites the red dye in addition to the blue dye, and vice versa. This effect interferes with the measurement results in the case of specific applications. Temporally gating the detection signals, it is possible also to assign to the detectors the laser pulse in addition to the wavelengths. This would mean that a detector responsible for the red light is temporally "blind" to those fluorescence signals which are generated by the temporally offset pulsed blue laser, and vice versa. Arbitrary further applications are considerable.

Figure 3:
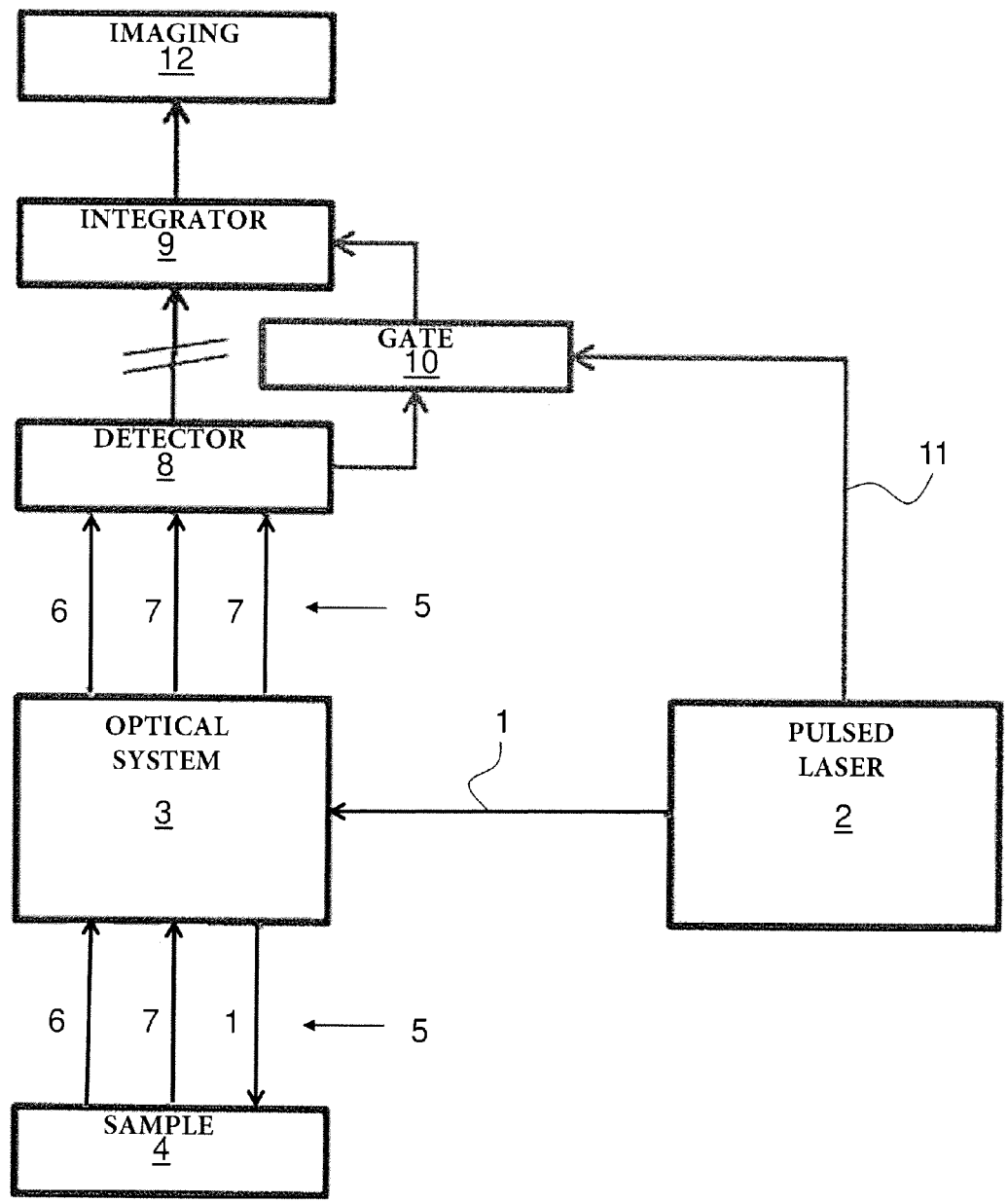
FIG. 3 shows, in a schematic view, the cooperation of the functional elements of an optical device which operates according to the inventive method.

FIG. 3 shows, in a schematic representation, the fundamental design and the mode of operation of an optical device which uses the inventive method.

The laser light 1 serving the purpose of fluorescence excitation is provided via a pulsed laser 2. The laser light 1 serving as excitation/illumination light reaches the sample 4 via a suitable optical system 3, said sample possibly being a biological sample in this case. The sample 4 is marked with fluorescing dyes. Accordingly, the laser light 1 excites the fluorescence dyes present in the sample 4 to emit light. The returning light, which is termed a detection light 5 below for the sake of simplicity, comprises, firstly, the fluorescent light 6 resulting from the emission of the fluorescence dyes and, secondly, reflected light 7 from the sample 4. The detection light 5 traverses or passes through the optical system 3, the reflected light 7 being supplemented by further instances of reflection and/or scattering from the optical system 3. Consequently, what reaches the detector 8 together with the fluorescent light 6 is reflected light 7 complemented by further instances of reflection and/or scattering.

By contrast with conventional optical devices, there is provided between the detector 8 and an integrator 9 which integrates or sums the electrical signals of the detector 8 a gate 10 with the aid of which it is possible, via a synchronization signal 11, for different signals to be filtered out or separated from one another in a defined temporal sequence from the total signals resulting from the detection light. In any event, the gate 10 is synchronized with the pulses of the excitation light, it being possible to tap the synchronization signal 11 directly at the laser driver.

Consequently, the only signals reaching the integrator 9 are those that are allowed or not filtered out via the gate 10, specifically in the case of the exemplary embodiment, selected here, of a confocal fluorescence microscope only the fluorescence signals which are summed in the integrator 9 and are used for the subsequent imaging 12.

With regard to further advantageous embodiments of the invention, reference is made to the general part of the description and to the attached patent claims in relation to the avoidance of repetitions.

Finally, it may be pointed out expressly that the above description of the invention serves merely to discuss the claimed teaching but does not restrict the latter to the description.

The foregoing description of preferred embodiments of the invention has been presented for purposes of illustration and description only. It is not intended to be exhaustive or to limit the invention to the precise form disclosed, and modifications and variations are possible and/or would be apparent in light of the above teachings or may be acquired from practice of the invention. The embodiments were chosen and described in order to explain the principles of the invention and its practical application to enable one skilled in the art to utilize the invention in various embodiments and with various modifications as are suited to the particular use contemplated. It is intended that the scope of the invention be defined by the claims appended hereto and that the claims encompass all embodiments of the invention, including the disclosed embodiments and their equivalents.

LIST OF REFERENCE NUMERALS

1 Laser light
2 Pulsed laser
3 Optical system
4 Sample, biological sample
5 Detection light
6 Fluorescent light (part of 5)
7 Reflected light (part of 5)
8 Detector
9 Integrator
10 Gate, gating
11 Synchronization signal
12 Imaging

What is claimed is:

1. A method for separating detection signals in a beam path of a fluorescent microscope, including a photon-counting detector for detecting an optical signal including fluorescent light, wherein the detection signals are signals resulting from fluorescent light and from reflected light or scattered light that strikes the photon-counting detector in the beam path, different of the detection signals being formed in a defined temporal sequence, the method comprising:

providing pulsed excitation light to excite the fluorescent light from a sample;
performing a suppression or separation of the detection signals on the basis of the temporal sequence;
integrating or summing electrical signals resulting from photons impinging on the photon-counting detector in a downstream integrator and being assigned to pixels;
filtering out reflection signals between the photon-counting detector and the integrator via a gate, triggered by a gating signal, the gate being synchronized with the pulsed excitation light, wherein the triggering by the gating signal is performed on an edge of a photon-counting signal of the photon-counting detector detecting the optical signal including fluorescent light.

2. The method according to claim 1, wherein fluorescence signals are used for measurements in the field of fluorescence correlation spectroscopy (FCS) or in fluorescence lifetime microscopy (FLIM technique), or fluorescence signals are used for imaging in confocal fluorescence microscopy.

3. The method according to claim 1, wherein synchronization is performed using a synchronization signal which is tapped directly at a laser driver, or by a synchronization signal determined from excitation light via the photon-counting detector.

4. The method according to claim 1, wherein the gating signal is temporally calibrated to a fluorescence signal.

5. The method according to claim 4, wherein calibration of the gating signal is performed by adapting a cable length between a laser and the gate.

6. The method according to claim 4, wherein the gating signal is calibrated by a variable electronic delay of a synchronization signal.

7. The method according to claim 6, wherein the electronic delay of the synchronization signal is calibrated by software.

8. The method according to claim 3, wherein at least two synchronization signals are provided in order to supply at least two detectors with different detection light.

9. The method according to claim 1, wherein an alternately pulsed light source is used as a light source for the pulsed excitation light.

10. The method according to claim 1, wherein a white light laser is used as a light source for the pulsed excitation light.

11. The method according to claim 1, wherein excitation is performed sequentially or simultaneously with a plurality of defined laser lines.

12. The method according to claim 1, wherein fluorescence signals based on the fluorescent light are used for measurements or imaging.

* * * * *

UNITED STATES PATENT AND TRADEMARK OFFICE
CERTIFICATE OF CORRECTION

PATENT NO.        : 9,651,765 B2
APPLICATION NO.   : 13/208387
DATED             : May 16, 2017
INVENTOR(S)       : Frank Schreiber It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1449 days.

Signed and Sealed this
Twenty-fifth Day of September, 2018

Andrei Iancu
*Director of the United States Patent and Trademark Office*